United States Patent
Teufelberger et al.

[11] Patent Number: 5,688,122
[45] Date of Patent: Nov. 18, 1997

[54] CHUCKING DEVICE FOR A DENTAL TOOL

[75] Inventors: Gunter Teufelberger, Bürmoos; Rudolf Schwaiger, Ostermiething, both of Austria

[73] Assignee: Dentalwerk Bürmoos Gesellschaft m.b.H., Bürmoos, Austria

[21] Appl. No.: 498,533

[22] Filed: Jul. 5, 1995

[30] Foreign Application Priority Data

Aug. 1, 1994 [AT] Austria .................... 1514/94

[51] Int. Cl.⁶ .................................. A61C 1/14
[52] U.S. Cl. .......................... 433/127; 433/129
[58] Field of Search ................... 433/127, 129; 279/47, 51; 81/477, 479, 478, 480, 481

[56] References Cited

U.S. PATENT DOCUMENTS

| | | | |
|---|---|---|---|
| 3,671,050 | 6/1972 | Anderson et al. | 279/47 |
| 3,672,060 | 6/1972 | Eibofner et al. | 32/26 |
| 3,685,845 | 8/1972 | Fischer et al. | 279/5 |
| 4,781,589 | 11/1988 | Bareth | 433/127 |
| 4,874,314 | 10/1989 | Fleer et al. | 433/127 |
| 5,074,789 | 12/1991 | Shibata | 433/127 |
| 5,165,896 | 11/1992 | Hain et al. | 433/129 |
| 5,383,785 | 1/1995 | Brugger | 433/129 |

FOREIGN PATENT DOCUMENTS 0273259 3/1991 European Pat. Off. .

Primary Examiner—Cary E. O'Connor
Attorney, Agent, or Firm—Friedrich Kueffner

[57] ABSTRACT

A chucking device for a dental tool in a dental handpiece or angle head includes a clamping sleeve with resilient tongues. The resilient tongues of the clamping sleeve are arranged at a distance from each of the two ends of the clamping sleeve. On the side on which an actuating member for the resilient tongues is provided, the internal width of the clamping sleeve is greater than the external diameter of the tools to be used. The actuating member for the resilient tongues is an essentially tubular member whose external diameter corresponds to the internal width of the clamping sleeve and whose internal diameter corresponds to the external diameter of the tools to be used.

8 Claims, 4 Drawing Sheets

CHUCKING DEVICE FOR A DENTAL TOOL

BACKGROUND OF THE INVENTION

1. Field of the Invention

The present invention relates to a chucking device for a dental tool in a dental handpiece or angle head.

2. Description of the Related Art

Chucking devices of this type must meet a number of conditions and requirements which contradict each other to some extent. On the one hand, the chucking device should hold the tool securely and safely, while, on the other hand, it should be possible to disengage the chucking device without the application of a great force, so that it is easier for the user of the chucking device to exchange the tool. Since it should be possible to disengage the chucking device without requiring tools and preferably by means of a pushbutton, the chucking device must have such a configuration that it can be actuated by means of such a pushbutton. In addition, the chucking device should be small and it should be suitable for very high rates of rotation.

In principle, the following chucking devices are known in the art:

1. One or more spring-loaded conical collet chucks for fixing the tool and for guiding the tool;
2. spring sleeves which are separated along a generatrix of a cylindrical holding portion and whose ends are constructed conically, so that, for carrying out the disengagement, the ends can be pressed apart from each other against the inherent springiness thereof by means of an internal cone of the actuating member; and
3. clamping sleeves which are slotted several times at an end thereof, wherein the clamping sleeves guide the tool along the non-slotted portion and wherein the clamping sleeves clamp the tool in the slotted portion by means of resilient tongues and wherein the clamping sleeves are spreadable in the slotted portion by means of an internal cone of an actuating member.

The present invention relates to the type of chucking devices mentioned last which is known, for example, from EP-B 0 273 259.

The disadvantages of such chucking devices are particularly the dynamic behavior of the clamping sleeves which is caused, in turn, by the required geometric configuration of the clamping end portion. In order to make it possible to bend the clamping tongues outwardly when disengaging the clamping sleeves, it is necessary that the external sleeve which is placed in the clamping sleeve has in the clamping portion in radial direction a distance from the outer surface of the clamping tongues.

However, this means that, during the operation of the dental instrument and because of the extremely high rates of rotation, vibrations and unbalanced masses occur in this area as a result of the always existing eccentricities and inaccuracies of manufacture. These vibrations and unbalanced masses are propagated to the working end of the tool and are painful for the patient and unpleasant for the user of the dental instrument.

In addition, because of the necessary relatively long axial extension of the slots which divide the clamping sleeve into the individual resilient tongues, the guide portion of the clamping sleeve must be relatively short, so that mounting and guidance of the tool is not fully satisfactory because of the short axial extension of the guide area.

In this connection, reference is made to the aforementioned EP-B 0 273 259 which shows in FIG. 1 that the guide portion of the clamping sleeve has a length which is less than a quarter of the axial extension of the head; in view of the forces which occur during operation, this short length of the clamping sleeve is a disadvantage.

SUMMARY OF THE INVENTION

Therefore, it is the primary object of the present invention to provide a chucking device of the above-described type in which the disadvantages described above are eliminated.

In accordance with the present invention, the resilient tongues of the clamping sleeve are arranged at a distance from each of the two ends of the clamping sleeve. On the side on which the actuating member for the resilient tongues is provided, the internal width of the clamping sleeve is greater than the external diameter of the tools to be used. The actuating member for the resilient tongues is an essentially tubular member whose external diameter corresponds to the internal width of the clamping sleeve and whose internal diameter corresponds to the external diameter of the tools to be used.

The configuration according to the present invention makes it possible to mount and guide the tools even beyond the resilient tongues, so that it is possible to utilize more than 70% of the axial extension of the instrument head for the guidance of the tool shaft. The mechanical and dynamic consequences of the configuration are immediately apparent to those skilled in the art and do not require further explanation.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
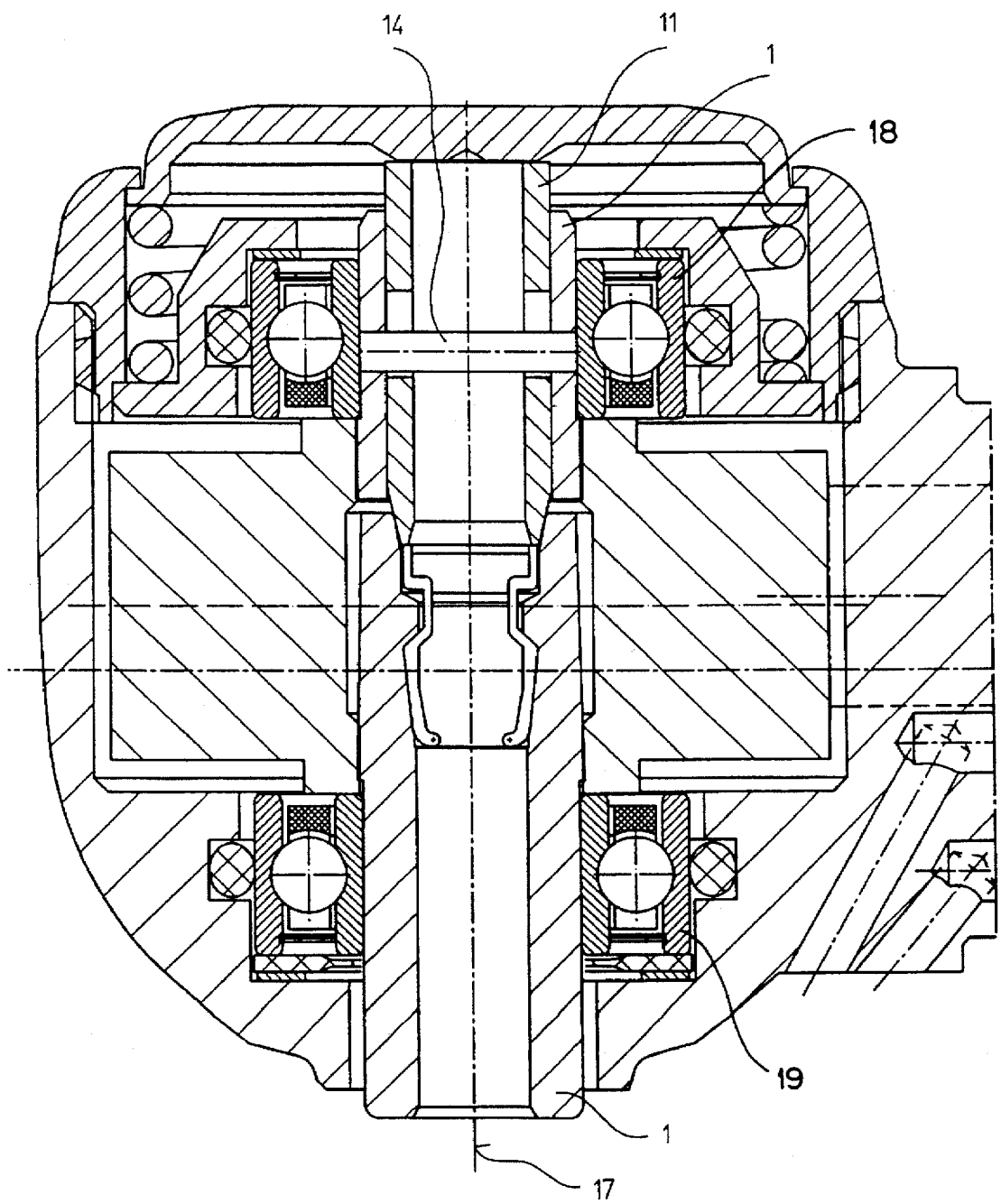
FIG. 1 is a sectional view showing the head piece of an angle piece with a chucking device according to the present invention.
Figure 2:
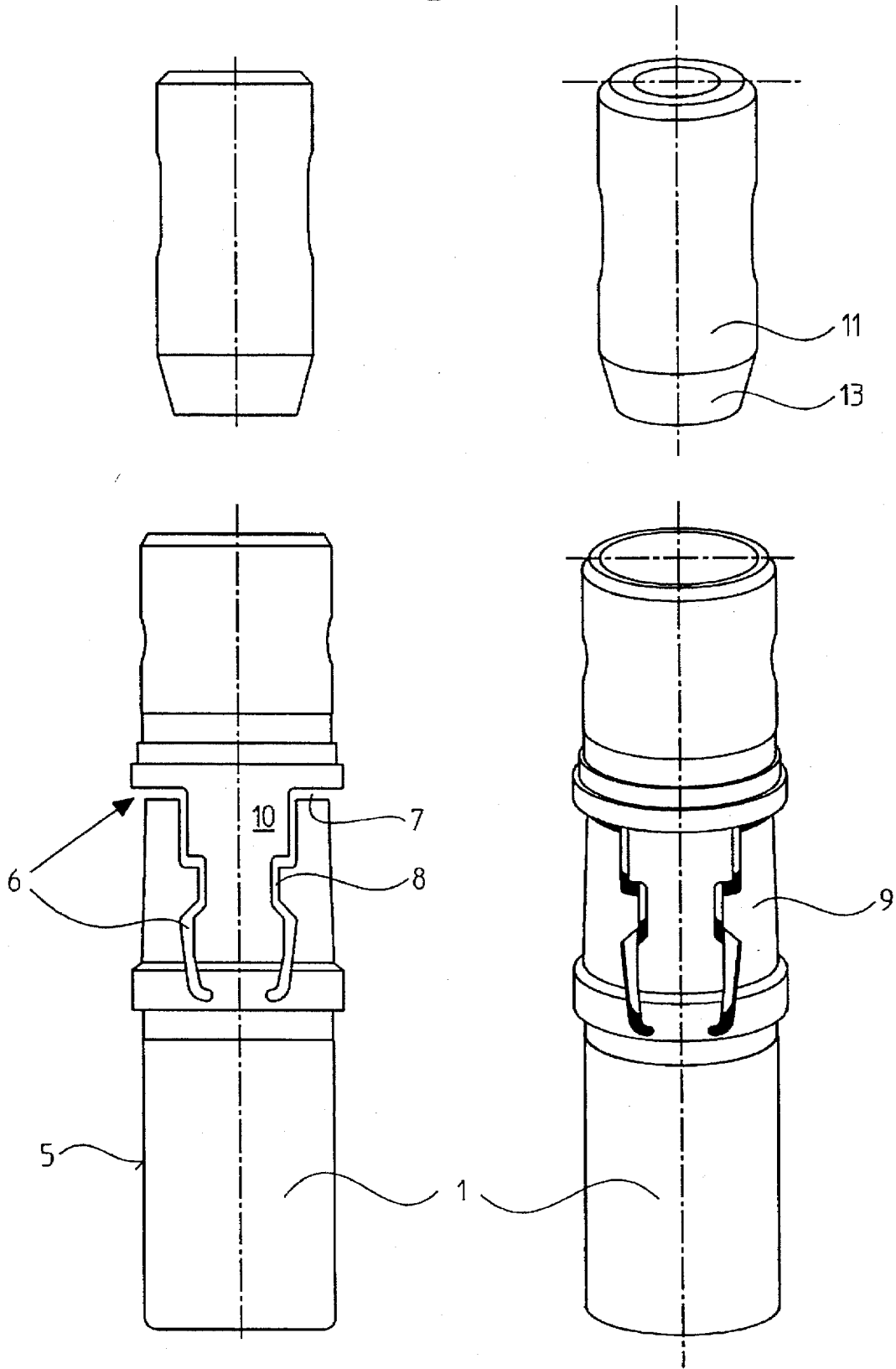
FIG. 2 contains a side view and a perspective top view of a clamping sleeve according to the present invention including actuating member.

In the specification and the claims, the references to top and bottom are used in such a way as it corresponds to the manipulation of the instrument in the position illustrated in FIG. 1. Thus, the free end of the tool, not shown, is at the bottom and the pushbutton of the instrument is at the top.

FIG. 1 of the drawing shows the head of a dental instrument which includes a chucking device according to the present invention. The chucking device has an axis 17. The chucking device includes a clamping sleeve 1 which has essentially three portions which are arranged adjacent to each other in axial direction, as is particularly clear from FIG. 3. The three portions are a lower guide portion 2, a middle clamping portion 3 and an upper guide portion 4.

As illustrated in FIG. 1, the head of the dental instrument includes roller bearings 18 and 19, wherein the outer surface of the roller bearing 18 is attached to the dental instrument and the inner surface of the roller bearing 18 is in direct contact with the clamping sleeve 1 in a portion of the clamping sleeve 1 receiving an actuating member 11, and wherein the outer surface of the roller bearing 19 is attached to the dental instrument and the inner surface of the roller bearing 19 is in direct contact with the clamping sleeve 1 in an axial portion of the clamping sleeve 1 facing away from the portion receiving an actuating member 11.

The lower guide portion 2 has an internal width or internal diameter which corresponds to the external diameter of the shaft of the tool to be used in such a way that it guides the tool shaft with the accuracy required and expected in the field of dental medicine.

The clamping portion 3 has slots 6 which extend starting from the surface 5 of the clamping sleeve 1 through the wall of clamping sleeve 1. The slots essentially have two portions: a first radially extending portion 7 and a second portion 8 which extends essentially parallel to the axis.

The axial extension of the slots 6 determines the position and size of the clamping portion 3 of the clamping sleeve 1: the specific configuration of the preferably two slots 6 produces resilient tongues 9 which are connected to the lower guide portion 2 along a circumferential section, while the tongues 9 are separated from the upper guide portion 4 by the radial portion 7 of the slots. As a result, it is possible to bend the resilient tongues 9 in accordance with the configuration of the slots radially inwardly with their ends facing the upper guide portion 4, so that, as a result, the resilient tongues are provided with their clamping property for the tool shaft to be inserted.

The situation is different with respect to the webs 10 which exist between the resilient tongues 9. The webs 10 are connected over a portion of the sleeve circumference to the lower guide portion 2 and the webs 10 are connected through an essentially analogous portion to the guide portion 4. The webs 10 ensure that the clamping sleeve 1 is a single component.

Figure 3:
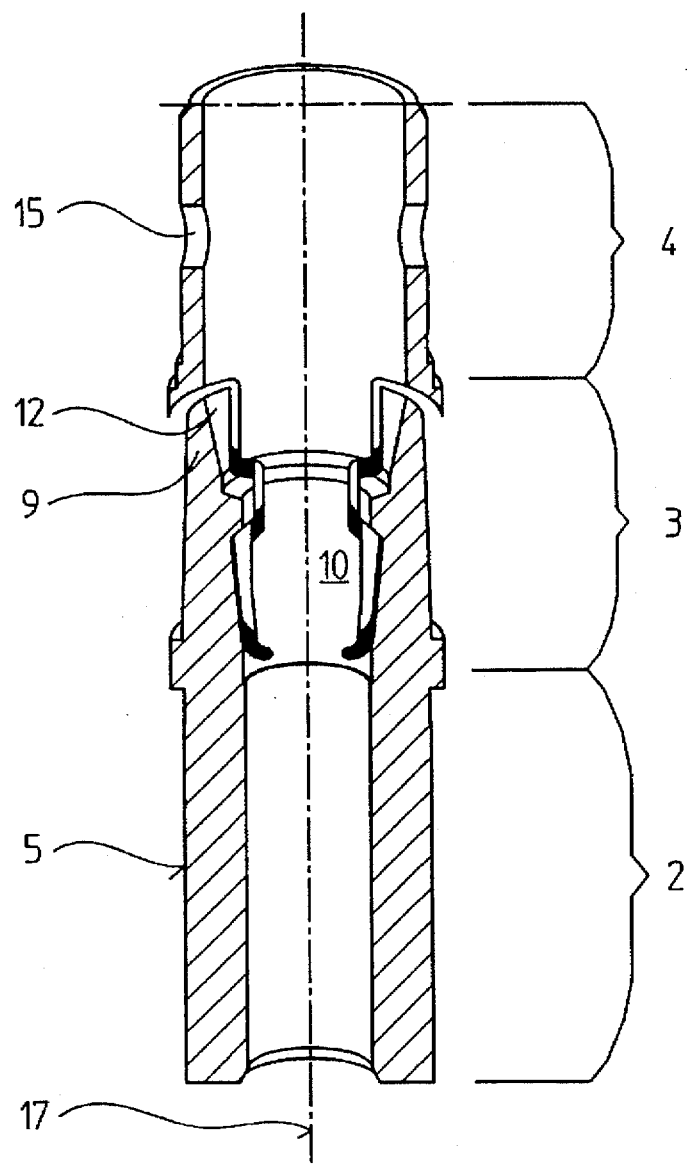
FIG. 3 is a sectional view of the clamping sleeve taken in the plane of the drawing of FIG. 2b.
Figure 5:
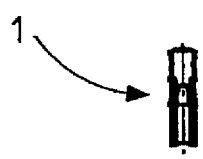
FIG. 5 shows the clamping sleeve of FIG. 3 in actual size.
Figure 4:
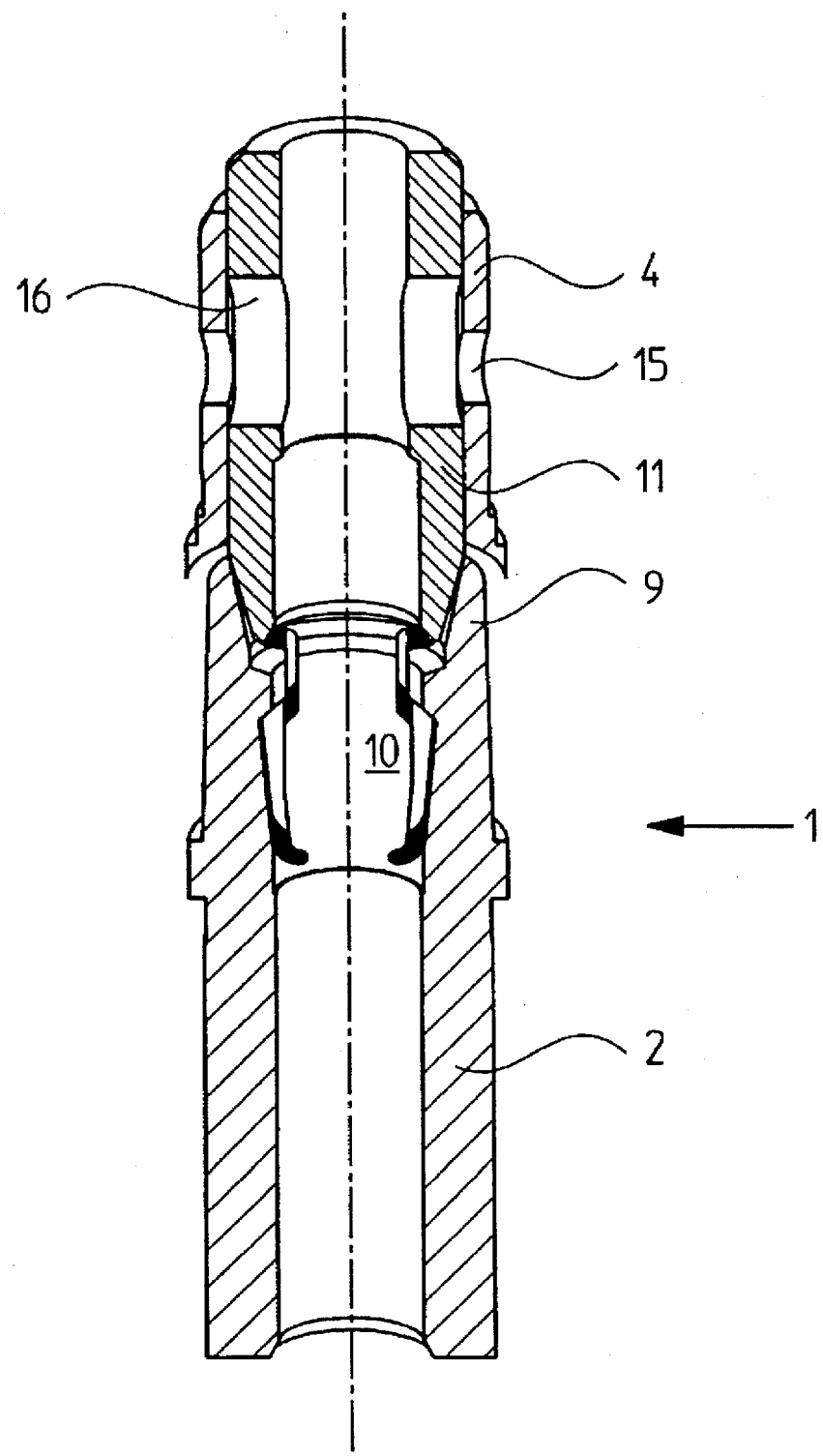
FIG. 4 is a sectional view, similar to FIG. 3, shown with the actuating member being inserted in the clamping sleeve.

Since, as particularly shown in FIGS. 3 and 4, the internal width of the upper guide portion 4 is greater than the internal width of the lower guide portion 2, it is possible to quickly insert the actuating member 11 into the upper guide portion 4, wherein the actuating member 11 has an internal diameter which corresponds to the internal diameter of the lower guide portion 2.

As a result of this configuration, it is possible to insert the shaft of a tool through the clamping portion 3 of the clamping sleeve 1 to the upper guide portion 4 where the tool shaft is guided by the actuating member.

As is clear particularly from FIGS. 1 and 4, the resilient tongues 9 are provided at their free ends with an internal cone 12 which interacts with an external cone 13 of the actuating member 11 when the actuating member 11 is displaced, so that it pushes the resilient tongues 9 radially outwardly against the inherent initial tension thereof and releases the tool shaft as a result.

FIG. 1 shows a securing pin 14. The securing pin 14 extends radially and serves to secure the actuating member 11 in axial direction as well as in circumferential direction. The securing pin 14 extends through a corresponding opening 15 of the clamping sleeve 1 and through an axially oriented oblong hole 16 of the actuating member 11, as shown in FIG. 4.

The securing pin 14 simultaneously serves as a stop for the tool shaft to be inserted. Accordingly, the tool is guided in the area of the lower end of the clamping sleeve 1 to the clamping portion 3 and subsequently in the area of the upper end of the clamping portion 3 to the stop at the securing pin 14. Since the middle portion over the length of insertion of the tool provides the smallest contribution mechanically as well as dynamically for the tool guidance and since, moreover, the clamping device also provides an albeit small guidance in this area, the entire length between the clamping sleeve 1 and the securing pin 14 can be considered the length of guidance, wherein this length of guidance corresponds to 70% of the axial extension of the head of the dental instrument. Consequently, the present invention makes it possible that the relative length of guidance is increased almost threefold.

The slots 6 are advantageously manufactured by spark erosion by means of an appropriately guided wire, so that the aligned arrangement of the two slot portions located circumferentially next to each other results in the two slots.

Of course, it is also possible to manufacture the slots by means of unilaterally mounted wires, wherein a radial orientation of the slots is possible.

Certainly, it is also possible to provide more than two resilient tongues 9. However, it is necessary in this connection to consider the actual size of the clamping sleeve 1 which has a length of only about 13 mm and an external diameter of only about 3 mm. When these dimensions are taken into consideration, it is apparent that the two slots 6 and the wall thickness changes controlling the stiffness of the resilient tongues 9 can only be produced by utilizing the most advanced techniques and the careful observation of all technological parameters.

The invention has been explained in connection with an angle head. However, it is of course possible to provide hand pieces with axially extending tool holders with the device according to the invention. For this purpose, it is only necessary to connect in a conventional manner the actuating member 11 to a handle provided on the instrument, as this is done in known chucking devices and, therefore, does not form part of the present invention.

Instead of using the securing pin 14, the actuating member 11 can also be secured in axial and circumferential direction relative to the clamping sleeve 1, for example, by means of resilient tongues which engage in recesses of the respectively other part. The securing pin 14 provides the advantage that it is robust, simple and reliable and that it simultaneously serves as a stop for the tool shaft.

It should additionally be noted with respect to FIG. 1 that the illustrated situation, in which the upper end face of the actuating member 11 comes into contact with the lower surface of the pushbutton, does not correspond to the position of operation; rather, during operation no contact exists between these two surfaces. This contact only occurs during the tool exchange after a short movement of the button which causes the actuating member to be displaced downwardly, wherein the oblong hole 16 may serve as a limitation of the pressing movement if no other stop is provided, for example, on the pushbutton itself.

The mechanical stability of the clamping sleeve 1 makes it possible to omit the outer sleeve for the clamping sleeve which is always necessary in the state of the art. Consequently, the wall thickness of the sleeve, which simultaneously serves as the guide sleeve, can be increased. This facilitates the manufacture of the sleeve, on the one hand, and contributes further to the strength, on the other hand. Finally, since a structural component is omitted, the dimensions of the entire chucking device and, thus, of the head of the dental instrument, are reduced.

The present invention is not limited to the illustrated example. Thus, as already mentioned, the clamping sleeve may have more than two resilient tongues. If it is required for whatever reason, an outer sleeve may be provided at least in the lower area of guidance. Also, the actuating member may be constructed differently, for example, it may be composed only of tongues which interact with the resilient tongues of the clamping sleeve. The areas between these tongues may be constructed so as to be radially resilient, so that the end portion of the tool shaft is guided in a frictionally engaging manner and not in a positively locking manner.

It is also possible to utilize the chucking device according to the present invention in dental instruments which have a mechanical drive and not, as shown in FIG. 1, an air turbine.

The various features of novelty which characterize the invention are pointed out with particularity in the claims annexed to and forming a part of this disclosure. For a better understanding of the invention, its operating advantages attained by its use, reference should be had to the drawing and descriptive matter in which there are illustrated and described preferred embodiments of the invention.

I claim:

1. A chucking device for a dental tool in a dental handpiece or angle head, the dental tool including a shaft having an external diameter, the chucking device comprising a clamping sleeve having end faces and an axis, the clamping sleeve further having slots forming at least one resilient tongue, the at least one resilient tongue being located spaced from the end faces of the clamping sleeve, an essentially tubular actuating member being received in a portion of the clamping sleeve for moving the at least one resilient tongue between an initial position for clamping the tool shaft and a radially outwardly bent portion for releasing the tool shaft, the portion of the clamping sleeve having an internal width and the actuating member having an internal diameter and an external diameter, wherein the width of the portion of the clamping sleeve is greater than the external diameter of the tool shaft, and wherein the external diameter of the actuating member corresponds to the internal width of the portion of the clamping sleeve and the internal diameter of the actuating member corresponds to the external diameter of the tool shaft.

2. The chucking device according to claim 1, wherein the slots forming the at least one resilient tongue extend, starting from an outer surface of the clamping sleeve, in a first essentially radially extending portion and a second portion extending essentially parallel to the axis of the clamping sleeve and connected to the first portion.

3. The chucking device according to claim 1, further comprising a radially extending securing pin for connecting with axial play the clamping sleeve to the actuating member.

4. The chucking device according to claim 3, wherein the actuating member has an axially extending oblong hole for receiving the securing pin.

5. The chucking device according to claim 1, wherein the clamping sleeve has another portion facing away from the portion receiving the actuating member, wherein the another portion has an internal width which corresponds essentially to the external diameter of the tool shaft.

6. The chucking device according to claim 1, wherein an outer surface of a roller bearing is attached to the dental handpiece, and wherein an inner surface of the roller bearing directly contacts the clamping sleeve in the portion of the clamping sleeve receiving the actuating member.

7. The chucking device according to claim 1, wherein an outer surface of a roller bearing is attached to the dental handpiece, and wherein an inner surface of the roller bearing directly contacts the clamping sleeve in an axial portion of the clamping sleeve facing away from the portion receiving the actuating member.

8. The chucking device according to claim 1, wherein the clamping sleeve has an axial length which is at least 50% of a length of the head of the dental tool.

* * * * *